United States Patent
Donnelly et al.

(10) Patent No.: US 8,956,410 B2
(45) Date of Patent: *Feb. 17, 2015

(54) FLEXIBLE TIBIAL SHEATH

(71) Applicant: DePuy Mitek, LLC, Raynham, MA (US)

(72) Inventors: Lisa M. Donnelly, Wayland, MA (US); Nathan Cauldwell, Attleboro, MA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/788,872

(22) Filed: Mar. 7, 2013

(65) Prior Publication Data

US 2013/0184819 A1    Jul. 18, 2013

Related U.S. Application Data

(60) Continuation of application No. 12/025,927, filed on Feb. 5, 2008, now Pat. No. 8,435,293, which is a division of application No. 11/935,653, filed on Nov. 6, 2007, now Pat. No. 7,699,893, which is a continuation of application No. 10/608,899, filed on Jun. 27, 2003, now Pat. No. 7,309,355.

(51) Int. Cl.
*A61F 2/08* (2006.01)
*A61B 17/08* (2006.01)

(52) U.S. Cl.
CPC ........ *A61F 2/0811* (2013.01); *A61F 2002/0835* (2013.01); *A61F 2002/0858* (2013.01); *A61F 2002/0888* (2013.01)
USPC ..................... 623/13.14; 623/13.15; 606/309; 606/313; 606/314

(58) Field of Classification Search
CPC ................. A61F 2002/0858; A61F 2002/0835

USPC ........... 623/13.11–13.15; 606/309, 313, 314; 411/44, 57.1, 63, 66, 69
See application file for complete search history.

(56) References Cited

U.S. PATENT DOCUMENTS 3,600,765 A * 8/1971 Rovinsky et al. ............ 24/122.6
3,896,504 A * 7/1975 Fischer ...................... 623/22.36
(Continued)

FOREIGN PATENT DOCUMENTS

| EP | 1 297 799 A2 | 4/2003 |
| FR | 2725615 A1 | 4/1996 |

(Continued)

OTHER PUBLICATIONS

Japanese Office Action for JP Pat. App. No. 2004-188326 mailed May 25, 2010 (English Translation, 4 pages).

(Continued)

*Primary Examiner* — David H Willse
*Assistant Examiner* — Javier Blanco

(57) ABSTRACT

A radially expandable sheath is provided having a substantially closed distal end with at least two sidewalls extending proximally therefrom and defining a central lumen. Each sidewall can have a substantially concave outer surface adapted to seat a graft member, and each side wall is at least partially separated by a longitudinally oriented slot that extends from a proximal end along a substantial length of each sidewall. The slot preferably terminates at a position just proximal to the distal end. The device can also include a sheath expander that is adapted to be disposed in the central lumen of the radially expandable sheath and that is configured to flex the sidewalls to radially expand the sheath so as to fix a graft member within a bone tunnel.

18 Claims, 4 Drawing Sheets

(56) References Cited

U.S. PATENT DOCUMENTS

| | | | |
|---|---|---|---|
| 4,474,516 A * | 10/1984 | Schiefer | 411/44 |
| 4,708,132 A | 11/1987 | Silvestrini | |
| 4,878,791 A * | 11/1989 | Kurihara et al. | 411/55 |
| 5,137,395 A * | 8/1992 | McCartney | 405/259.3 |
| 5,632,748 A | 5/1997 | Beck, Jr. et al. | |
| 5,707,395 A | 1/1998 | Li | |
| 5,746,745 A * | 5/1998 | Abele et al. | 623/1.11 |
| 5,899,938 A | 5/1999 | Sklar et al. | |
| 5,906,632 A | 5/1999 | Bolton | |
| 6,099,530 A | 8/2000 | Simonian et al. | |
| 6,328,758 B1 * | 12/2001 | Tornier et al. | 606/232 |
| 6,379,361 B1 | 4/2002 | Beck, Jr. et al. | |
| 6,554,862 B2 | 4/2003 | Hays et al. | |
| 6,652,560 B1 | 11/2003 | Gerke et al. | |
| 6,887,271 B2 | 5/2005 | Justin et al. | |
| 7,309,355 B2 | 12/2007 | Donnelly et al. | |
| 7,699,893 B2 | 4/2010 | Donnelly et al. | |
| 8,317,863 B2 | 11/2012 | Cauldwell et al. | |
| 8,435,293 B2 | 5/2013 | Donnelly et al. | |
| 2001/0007074 A1 | 7/2001 | Strobel et al. | |
| 2002/0007182 A1 | 1/2002 | Kim | |
| 2002/0055780 A1 | 5/2002 | Sklar | |
| 2002/0065390 A1 | 5/2002 | Kanada et al. | |
| 2002/0072797 A1 | 6/2002 | Hays et al. | |
| 2002/0165546 A1 | 11/2002 | Goble et al. | |
| 2003/0065390 A1 | 4/2003 | Justin et al. | |
| 2004/0267361 A1 | 12/2004 | Donnelly et al. | |
| 2008/0133007 A1 | 6/2008 | Donnelly et al. | |
| 2008/0161806 A1 | 7/2008 | Donnelly et al. | |
| 2010/0161055 A1 | 6/2010 | Donnelly et al. | |

FOREIGN PATENT DOCUMENTS

| | | |
|---|---|---|
| GB | 2173565 A | 10/1986 |
| JP | 05-300917 A | 11/1993 |
| WO | 02/32345 A2 | 4/2002 |
| WO | 03/028591 A1 | 4/2003 |

OTHER PUBLICATIONS

Japanese Office Action for JP Pat. App. No. 2004-188326 mailed May 25, 2010 (4 pages).

* cited by examiner

FLEXIBLE TIBIAL SHEATH

CROSS REFERENCE TO RELATED APPLICATIONS

This application is a continuation of U.S. patent application Ser. No. 12/025,927 filed on Feb. 5, 2008 and entitled "Flexible Tibial Sheath," now U.S. Pat. No. 8,435,293, which is a divisional of U.S. patent application Ser. No. 11/935,653 filed on Apr. 20, 2010 and entitled "Flexible Tibial Sheath," now U.S. Pat. No. 7,699,893, which is a continuation of U.S. patent application Ser. No. 10/608,899 filed on Jun. 27, 2003 and entitled "Flexible Tibial Sheath," now U.S. Pat. No. 7,309,355, which are hereby incorporated by reference their entireties.

FIELD OF THE INVENTION

The present invention relates to ligament fixation devices and methods, and more particularly to devices and methods for anchoring ligaments within a bone tunnel.

BACKGROUND OF THE INVENTION

Ligaments are tough bands of tissue which serve to connect the articular extremities of bones, or to support or retain organs in place within the body. Ligaments are typically composed of coarse bundles of dense white fibrous tissue which are disposed in a parallel or closely interlaced manner, with the fibrous tissue being pliant and flexible, but not significantly extensible.

In many cases, ligaments are torn or ruptured as a result of accidents or overexertion. Accordingly, various procedures have been developed to repair or replace such damaged ligaments. For example, in the human knee, the anterior and posterior cruciate ligaments (i.e., the ACL and PCL) extend between the top end of the tibia and the bottom end of the femur. The ACL and PCL cooperate, together with other ligaments and soft tissue, to provide both static and dynamic stability to the knee. Often, the ACL is ruptured or torn as a result of, for example, a sports-related injury. Consequently, various surgical procedures have been developed for reconstructing the ACL so as to restore normal function to the knee.

In many instances, the ACL may be reconstructed by replacing the ruptured ACL with a graft ligament. More particularly, with such procedures, bone tunnels are typically formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways known in the art so that the graft ligament extends between the femur and the tibia in substantially the same way, and with substantially the same function, as the original ACL. This graft ligament then cooperates with the surrounding anatomical structures so as to restore normal function to the knee.

Despite the above-identified advances in the art, there remains a need for a graft ligament anchor which is simple, easy to install, and inexpensive to manufacture, while providing secure, trouble-free anchoring of the graft ligament.

SUMMARY OF THE INVENTION

The present invention generally provides a graft fixation device for fixing a graft member within a bone tunnel. In one embodiment, the device includes a bioabsorbable, radially expandable sheath having a substantially closed distal end with at least two sidewalls extending proximally therefrom and defining a central lumen. Each sidewall is at least partially separated by a longitudinally oriented slot extending from a proximal end along a substantial length of each sidewall and terminating at a position proximal to the distal end. The shape of the sidewalls can vary, but preferably each sidewall has a substantially concave outer surface adapted to seat a graft member. Each sidewall can optionally include surface features formed within the concave outer surface thereof. The device can also include a bioabsorbable sheath expander, e.g., a tapered screw, adapted to be disposed in the central lumen of the radially expandable sheath and configured to flex the sidewalls to radially expand the sheath so as to fix a graft member within a bone tunnel. In an exemplary embodiment, the sheath expander has a largest diameter that is greater than a largest inner diameter of the radially expandable sheath in an unexpanded state.

The radially expandable sheath can have a variety of configurations. In one embodiment, the distal portion of the radially expandable sheath, extending between a distal end of the longitudinally oriented slots and a distal end of the sheath, tapers to form a bullet-shaped distal tip. In another embodiment, at least two adjacent sidewalls are joined at a proximal end thereof by a stop member adapted to prevent over-insertion of the radially expandable sheath into a bone tunnel.

The configuration of the graft fixation device allows the device to be formed from a variety of materials, including materials having a low elasticity. In an exemplary embodiment, the graft fixation device is formed from one or more polymers or copolymers formed from monomers selected from the group consisting of lactic acid, glycolic acid, and caprolactone. In a more preferred embodiment, the material further includes tricalcium phosphate.

In yet another embodiment, a graft fixation device for fixing a graft member within a bone tunnel is provided. The device includes a bioabsorbable, radially expandable sheath having a substantially closed distal end with at least two sidewalls extending proximally therefrom and defining a central lumen. Each sidewall has a substantially concave outer surface adapted to seat a graft member, and each side wall is at least partially separated by a longitudinally oriented slot extending from a proximal end along a substantial length of each sidewall and terminating at a position proximal to the distal end.

In other aspects, a graft fixation kit for fixing a graft member within a bone tunnel is provided. The kit includes a bioabsorbable expandable sheath having proximal and distal ends with at least two sidewalls extending therebetween and defining a central lumen. Each sidewall is at least partially separated by a longitudinally oriented slot extending from the proximal end and terminating at a position just proximal to the distal end, and each sidewall has an outer surface adapted to seat a graft member. The kit further includes a plurality of sheath expanders of varying sizes, each being disposable in the central lumen of the expandable sheath and configured to flex the sidewalls to radially expand the sheath so as to fix at least one graft member within a bone tunnel.

Methods for fixing a ligament graft in a bone tunnel are also provided.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein.

DETAILED DESCRIPTION OF THE INVENTION

Figure 1:
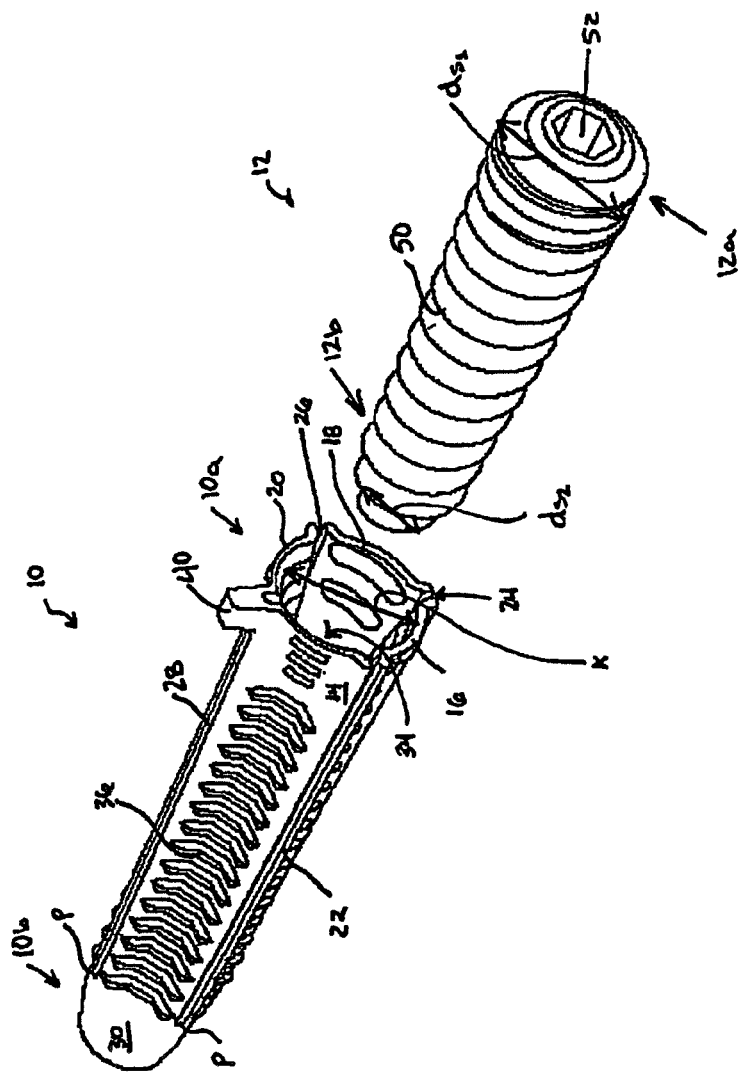
FIG. 1 is a perspective view of a radially expandable sheath and a sheath expander in accordance with one embodiment of the invention.

As shown in FIG. 1, the present invention generally provides a radially expandable sheath 10 for attaching a ligament graft to bone. In general, the expandable sheath has a substantially closed distal end with at least two sidewalls (FIG. 1 illustrates four sidewalls 14, 16, 18, 20) extending proximally therefrom and defining an inner lumen 34. Each sidewall 14, 16, 18, 20 can have a substantially concave outer surface adapted to seat a graft member, and each sidewall 14, 16, 18, 20 is at least partially separated by a longitudinally oriented slot 22, 24, 26, 28 that extends from a proximal end 10a along a substantial length of each sidewall 14, 16, 18, 20. The slots 22, 24, 26, 28 preferably terminate at a position just proximal to the distal end 10b of the sheath 10. The device can also optionally include a sheath expander 12 that is adapted to be disposed in the central lumen 34 of the radially expandable sheath 10 and that is configured to flex the sidewalls 14, 16, 18, 20 to radially expand the sheath 10 so as to fix a graft member within a bone tunnel.

A person skilled in the art will appreciate that a variety of implants having virtually any configuration can be used to expand the expandable sheath, and that sheath expander 12 is merely one embodiment of an implant that can be used with the expandable sheath. Moreover, the expandable sheath 10 can be used to attach a variety of materials to bone in a variety of medical procedures. Accordingly, the terms "graft" or "ligament graft," as used herein, are intended to include any number of natural and/or synthetic graft and/or tendon materials.

Figure 2:
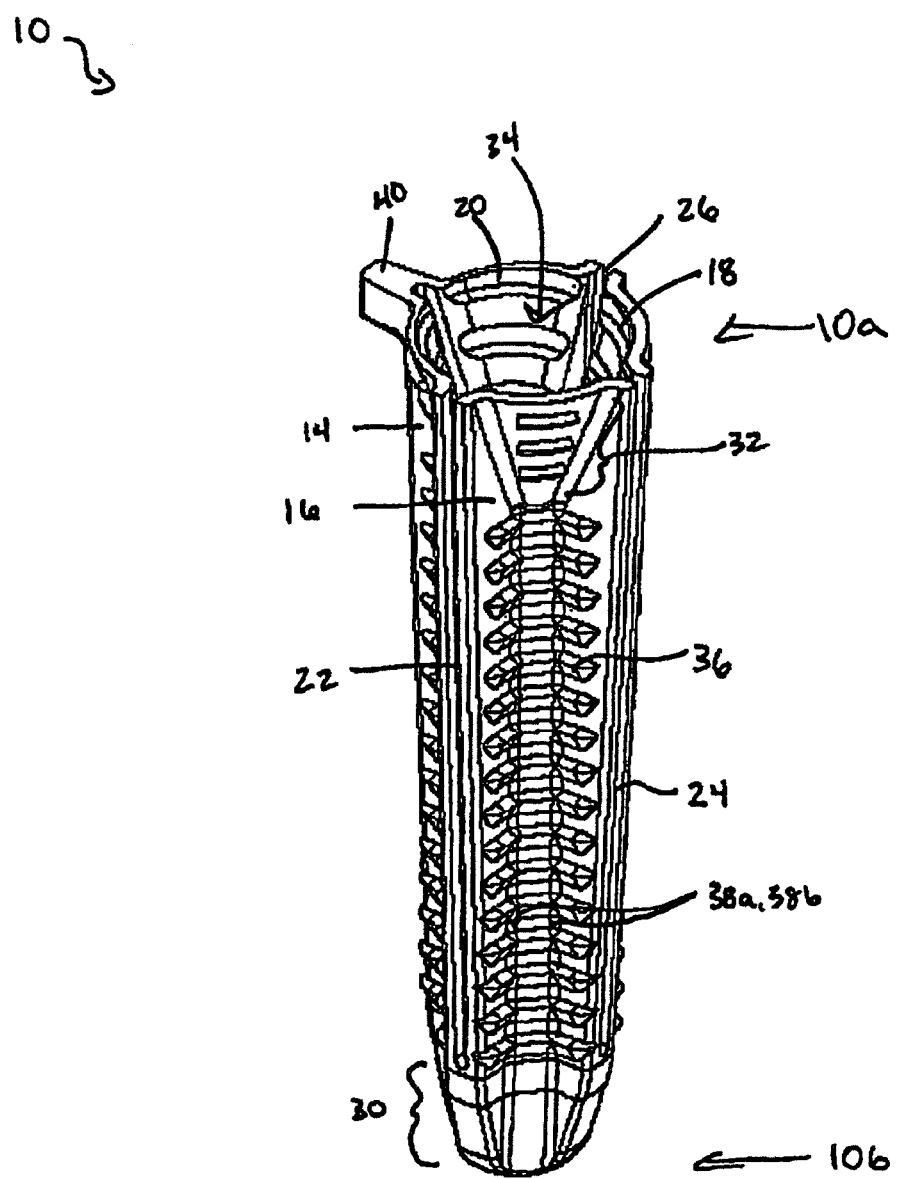
FIG. 2 is a perspective view of the radially expandable sheath shown in FIG. 1.
Figure 3A:
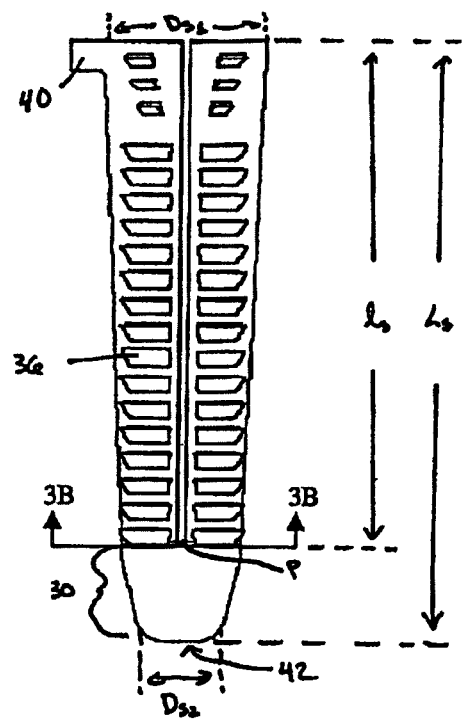
FIG. 3A is a side view of the radially expandable sheath shown in FIGS. 1 and 2.
Figure 3B:
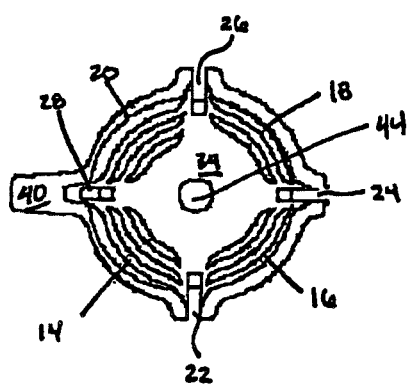
FIG. 3B is a cross-sectional view of the radially expandable sheath shown in FIG. 3A taken across line 3B-3B.

The expandable sheath 10 can have a variety of configurations, shapes, and sizes, but it should be adapted to expand within a bone tunnel to attach a ligament graft to bone. FIGS. 1-3B illustrate an exemplary embodiment of an expandable sheath 10 having proximal and distal ends 10a, 10b with four sidewalls 14, 16, 18, 20 extending therebetween. While four sidewalls 14, 16, 18, 20 are shown, a person skilled in the art will appreciate that the sheath 10 can have any number of sidewalls. The sheath 10 should, however, have at least two sidewalls to allow the sheath 10 to expand upon insertion of a sheath expander therein. Each sidewall 14, 16, 18, 20 preferably tapers from a proximal end 10a of the sheath to a distal end 10b of the sheath to form a sheath 10 having a bullet-shaped profile. As a result, the proximal end 10a of the sheath 10 defines the largest outer diameter or circumference $Ds_1$ of the sheath, and the distal end 10b defines the smallest outer diameter or circumference $Ds_2$ of the sheath, as shown in FIG. 3A. The sheath 10 also includes an inner diameter x which is the largest at its proximal end 10a and decreases towards its distal end 10b.

Each sidewall 14, 16, 18, 20 of the sheath 10 is preferably separated from an adjacent sidewall by a longitudinally oriented slot 22, 24, 26, 28 extending therebetween. Each slot 22, 24, 26, 28 can have the same length ls, or alternatively the length of each slot 22, 24, 26, 28 can vary with respect to each other. In an exemplary embodiment, each slot 22, 24, 26, 28 has the same length ls and originates at the proximal end 10a of the sheath 10 and extends along a substantial length Ls of the sheath 10 to allow the sidewalls 14, 16, 18, 20 to flex with respect to each other. Each slot 22, 24, 26, 28 preferably terminates at the same position P just proximal to the distal end 10b of the sheath to provide a slot-free distal tip 30. This termination point P defines the area at which each sidewall 14, 16, 18, 20 will bend during expansion of the sheath 10 by a sheath expander. Thus, while the termination point P can vary, the distance between the termination point P at the end of each slot 22, 24, 26, 28 and the distal end 10b of the sheath should be sufficient to provide structural integrity to the device such that the sidewalls 14, 16, 18, 20 do not break apart from one another or from the distal tip 30 during expansion.

Each sidewall 14, 16, 18, 20 of the sheath 10 can also have a variety of shapes and sizes. In an exemplary embodiment, each sidewall 14, 16, 18, 20 has a substantially concave outer surface that is adapted to seat a graft. The concave surface preferably extends along the length ls of each sidewall 14, 16, 18, 20. The proximal-most portion of each sidewall 14, 16, 18, 20, however, can include a flared region 32 (FIG. 2) to provide an enlarged opening to the inner lumen 34 to facilitate insertion of a sheath expander therein. Each sidewall 14, 16, 18, 20 can also include one or more surface features 36 formed on the concave surface to facilitate engagement of a graft between the sidewalls 14, 16, 18, 20 and the bone tunnel when the sheath 10 is implanted. The surface features 36 can have a variety of configurations, and can be formed on all or a portion of one or more of the sidewalls 14, 16, 18, 20. As shown in FIGS. 1-3A, the surface features 36 are formed from a series of transversely-oriented ridges 36 formed along a substantially portion of each sidewall 14, 16, 18, 20. The ridges 36 are effective to engage or grip the graft to prevent sliding movement of the graft with respect to the sheath 10. A person skilled in the art will appreciate that the sheath 10 can include a variety of different features to facilitate engagement between the sheath 10 and the graft.

Each sidewall 14, 16, 18, 20 can also include one or more longitudinal flexion regions to allow each sidewall 14, 16, 18, 20 to expand radially outward upon insertion of a sheath expander into the lumen 34 of the sheath 10. FIG. 2 illustrates flexion regions 38a, 38b on sidewall 16. As shown, the flexion regions 38a, 38b are formed from substantially parallel edges that extend along the length Ls of the sheath 10 and that define the concave shape of each sidewall 14, 16, 18, 20. The flexion regions can optionally be formed by thinning the material that forms each sidewall 14, 16, 18, 20 longitudinally in the region of desired flexion, and in one embodiment, may be one or more longitudinal grooves cut into each sidewall 14, 16, 18, 20. In use, the expansion of the sidewalls 14, 16, 18, 20 at the flexion regions 38a, 38b will retain the graft material disposed within the sidewall 14, 16, 18, 20 by an interference fit between the expanded sidewall 14, 16, 18, 20 and the bone tunnel wall.

While each sidewall 14, 16, 18, 20 is described as being separated by a longitudinally oriented slot, two or more sidewalls adjacent to one another can optionally include a stop member extending therebetween and adapted to prevent over-insertion of the sheath 10 into a bone tunnel. While the stop member can have a variety of configurations, FIGS. 1-3B illustrate an exemplary embodiment of a stop member 40 formed on the proximal-most end 10a of the sheath 10 and extending between two adjacent sidewalls, e.g., sidewalls 14 and 20, to connect the sidewalls 14, 20. The stop member 40 can have a variety of configurations, and in one embodiment, as shown, is a tab-like protrusion that extends outward from the circumference of the proximal end 10a of the sheath 10. As a result, the stop member 40 will abut the edge of a bone tunnel during insertion of the sheath 10 into the bone tunnel, thereby preventing over-insertion of the sheath 10.

While the stop member 40 connects two adjacent sidewalls, the stop member 40 can optionally be adapted to break upon insertion of a sheath expander into the sheath 10 to allow the sidewalls 14, 16, 18, 20 to expand. To ensure that breakage occurs at the proper location, the stop member 40 can include a weakened portion (not shown) formed at the desired breakage point. A person skilled in the art will appreciate that a variety of techniques can be used to achieve the desired breakage.

The distal tip 30 of the sheath can also have a variety of configurations, shapes and sizes. Since the distal tip 30 connects the four sidewalls 14, 16, 18, 20 to one another to provide structural integrity to the sheath 10, the distal tip 30 is preferably slot-free, and also preferably does not include any surface features 36 formed thereon. While the shape of the distal tip 30 can vary, the distal tip 30 preferably originates adjacent to the termination point P of each longitudinal slot 22, 24, 26, 8, and tapers toward the distal end 10b of the sheath 10. The distal tip 30 can optionally include a flattened distal-most surface 42 (FIG. 3A) that joins a distal-most end of each sidewall 14, 16, 18, 20 to one another. The edges (not shown) that connect the flattened surface 42 to each sidewall 14, 16, 18, 20 are preferably rounded to form a substantially rounded distal tip 30. The distal tip 30 can also optionally include a bore 44 (FIG. 3B) extending through the flattened surface 42 for receiving a guide wire to facilitate implantation of the device. A person skilled in the art will appreciate that the distal tip 30 of the sheath 10 can have virtually any shape and size, and can optionally be substantially open or closed.

Referring back to FIG. 1, a sheath expander 12 can be used to expand the expandable sheath 10 once the sheath 10 is inserted into a bone tunnel. While the sheath expander 12 can have virtually any configuration, FIG. 1 illustrates an exemplary embodiment of a sheath expander 12 in the form of a tapered screw. The screw 12 includes a proximal end 12a defining the largest diameter $ds_1$ of the screw, and a distal end 12b defining the smallest diameter $ds_2$ of the screw 12. Threads 50 are formed around the screw 12 and extend from the proximal end 12a to the distal end 12b. In use, the screw 12 is adapted to expand the expandable sheath 10, thus the largest diameter $ds_2$ of the screw 12 is preferably larger than the largest inner diameter x (FIG. 1) of the sheath 10, and more preferably it is at least as large as the largest outer diameter $Ds_1$ of the sheath 10. The expander screw 12 also preferably includes a socket 52 formed in the proximal end 12a thereof for receiving a driver tool, such as a hex wrench, that is effective to drive the screw 12 into the sheath 10. The expander screw 12 can also include a lumen (not shown) extending therethrough for receiving a guide wire to facilitate insertion of the screw 12 into the sheath 10. As previously stated, a person skilled in the art will appreciate the sheath expander 12 can have a variety of configurations, shapes, and sizes.

Figure 4A:
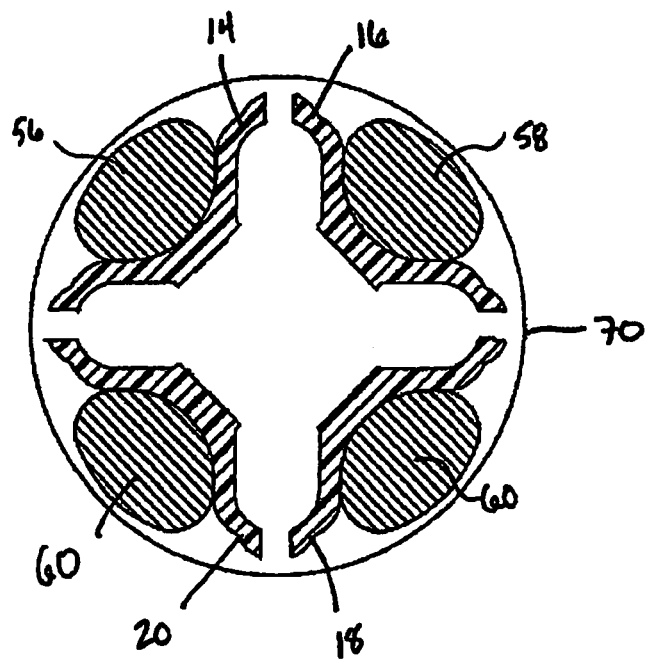
FIG. 4A is an illustration of a bone tunnel having four segments of a ligament graft and a radially expandable sheath disposed therein in an unexpanded position.
Figure 4B:
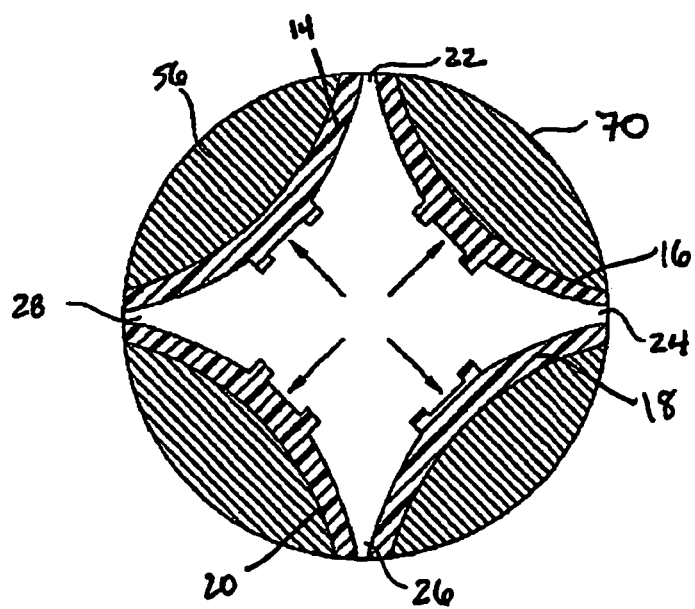
FIG. 4B is an illustration of the bone tunnel, ligament segments, and radially expandable sheath shown in FIG. 4A with the radially expandable sheath in the expanded position.

The expandable sheath 10 and sheath expander 12 can be used in a variety of medical procedures, but they are preferably used to anchor ligaments within a bone tunnel. In an exemplary embodiment, the device or system 10, 12 is used for tibial fixation of an anterior cruciate ligament graft. A bone tunnel is prepared in the patient's tibia, and the graft is separated into four tendon bundles, each of which is prepared by whip stitching a length of suture thereto. The graft is then passed through the tunnel and tensioned as necessary. While tensioning the graft, the expandable sheath 10 is inserted into the opening of the bone tunnel, preferably by sliding the sheath 10 along a guide wire extending through the tunnel. A mallet or other impacting device can be used to gently advance the sheath 10 into the tunnel. The stop member 40 will abut the opening of the tunnel when the sheath 10 is fully inserted. In this position, a graft bundle, which preferably includes four grafts 56, 58, 60, 62, as shown in FIG. 4A, is preferably seated within each sidewall 14, 16, 18, 20 of the expandable sheath 10. The sheath expander, e.g., tapered expander screw 12, is then slowly inserted into the inner lumen 34 of the sheath 10, using a driver tool, to expand the concave sidewalls 14, 16, 18, 20 of the sheath 10. As the sheath expander 12 is driven into the sheath 10, the concave sidewalls 14, 16, 18, 20 of the sheath 10 will deform toward a circular geometry to conform with an outer diameter of the expander 12, and thus to compress each tendon bundle 56, 58, 60, 62 against the bone tunnel wall 70, as shown in FIG. 4B. This will encourage rapid bony ingrowth into each bundle.

The sheath 10 of the present invention provides several advantages over prior art sheaths. In particular, the longitudinally oriented slots 22, 24, 26, 28 reduce or eliminate the risk of cracking or splitting during expansion. While some prior art sheaths provide a weakened portion adapted to rupture or break upon insertion, the sheath can crack at unintended portions. The slots 22, 24, 26, 28 of the sheath 10 of the present invention eliminate the need for the sheath 10 to crack during insertion of the sheath expander 12 therein since the longitudinal slots 22, 24, 26, 28 allow for expansion without cracking. The slots 22, 24, 26, 28 also allow the sheath 10 to be formed from a material having a relatively low elasticity, e.g., a brittle material. Since the sheath 10 does not need to be designed to break only at an intended location, the entire sheath 10 can be made from a brittle material. By way of non-limiting example, suitable materials include biocompatible, bioabsorbable polymers or copolymers formed of monomers selected from the group consisting of lactic acid, glycolic acid, and caprolactone. In a further embodiment, the material can also include tricalcium phosphate. The sheath 10 can also be formed from bioabsorbable glasses and ceramics (possibly containing calcium phosphates and other biocompatible metal oxides (i.e., CaO)). The sheath 10 can also be formed from metals, or it can comprise combinations of metals, bioabsorbable ceramics, glasses or polymers. In an exemplary embodiment, the sheath is formed from polylactic acid (PLA), tricalcium phosphate (TCP), and optionally polyglycolic acid (PGA), and/or polycaprolactone (PCL). More preferably, the sheath is formed from one of the following materials (all percentages are by volume unless otherwise indicated):

| | |
|---|---:|
| 70% PLA+30% TCP | (1) |
| 70% of a PGA/PLA mixture+30% TCP | (2) |
| 70% of a PLA/PCL mixture+30% TCP | (3) |
| 70% of a PGA/PCL/PLA mixture+30% TCP | (4) |

Further, the longitudinal slots 22, 24, 26, 28 facilitate the use of expanders 12 having a wider variety of sizes, including the use of expanders 12 having an outer diameter $ds_1$ or circumference at least as large as the diameter $Ds_1$ or circumference of sheath 10. In this way, a single sheath size may be stocked for a wide variety of procedures and intended bone tunnel sizes. In one embodiment, sheath 10 may be provided in a kit to surgeons in which a plurality of expanders having different sizes are provided for use with a single size sheath.

It is to be understood that the present invention is by no means limited to the particular constructions and methods herein disclosed and/or shown in the drawings, but also comprises any modifications or equivalents within the scope of the claims

What is claimed is:

1. A medical device, comprising:
    an outer member configured to be advanced into a hole formed in bone, the outer member having
        a distal tip defining a longitudinal length between proximal and distal ends thereof,
        a plurality of longitudinal sidewalls extending proximally from the proximal end of the distal tip, each of the sidewalls being configured to have a graft member seated against an exterior surface thereof, and each of the sidewalls being separated by a longitudinal slot such that the sidewalls and the slots are alternately arranged around a perimeter of the outer member, and
    a bore formed therein that extends distally from the proximal end of the outer member; and
    an inner member having a proximal end and a distal end, the distal end of the inner member being configured to be advanced into the bore when the outer member is positioned within the hole so as to
        cause each of the sidewalls along entire longitudinal lengths thereof to move radially outward relative to the distal tip,
        deform each of the sidewalls from a first cross-sectional shape transverse to a longitudinal axis of the outer member to a second cross-sectional shape transverse to the longitudinal axis of the outer member, the second cross-sectional shape being different from the first cross-sectional shape, and
        press each of the graft members against the bone within the hole.

2. The device of claim 1, wherein the exterior surface of each of the sidewalls is substantially concave at least when the sidewall has the first cross-sectional shape.

3. The device of claim 1, wherein the inner member is concentric with the outer member when disposed within the outer member.

4. The device of claim 1, wherein a maximum outer diameter of the inner member is larger than a maximum diameter of the bore.

5. The device of claim 1, wherein a maximum outer diameter of the inner member is at least as large as a maximum outer diameter of the outer member.

6. The device of claim 1, wherein the proximal end of the distal tip defines an area where each of the sidewalls is configured to bend when the distal end of the inner member is advanced into the bore when the outer member is positioned within the hole so as to cause each of the sidewalls to move radially outward relative to the distal tip.

7. The device of claim 1, wherein the distal end of the inner member being advanced into the bore when the outer member is positioned within the hole causes the bore to change from having a third cross-sectional shape to a fourth cross-sectional shape that is different from the third cross-sectional shape.

8. The device of claim 1, wherein the second cross-sectional shape is an arc of a circle.

9. The device of claim 1, wherein the distal tip is a closed tip.

10. The device of claim 1, wherein the distal tip has an opening formed therethrough that is in communication with the bore and that is configured to receive a guidewire therethrough.

11. The device of claim 1, wherein the inner member is bioabsorbable and the outer member is bioabsorbable.

12. The device of claim 1, wherein the distal tip does not deform in response to the inner member being fully distally advanced into the bore when the outer member is positioned within the hole.

13. A medical device, comprising:
    an outer member configured to be advanced into a hole formed in bone, the outer member having
        a proximal end and a distal end,
        an inner lumen extending longitudinally through at least a portion thereof,
        at least two longitudinal sidewalls extending along a partial longitudinal length of the outer member, each of the sidewalls having an outer surface configured to seat a graft member,
        at least two longitudinal openings that define empty space between adjacent ones of the sidewalls, and
        a non-expandable distal tip that is distal to the sidewalls and the openings, a proximal end of the distal tip defining a bend area where each of the sidewalls is configured to bend relative to the distal tip; and
    an inner member configured to be advanced into the inner lumen when the outer member is positioned within the hole so as to cause each of the sidewalls having the graft members seated therein to
        bend at the bend area relative to the distal tip in a direction away from a longitudinal axis of the inner member so as to fix the graft members within the hole, and
        deform in shape such that a greater surface area of the outer surface of each of the sidewalls directly contacts the graft member seated therein than when the graft members are seated in the outer surfaces before the inner member is advanced into the inner lumen of the outer member.

14. The device of claim 13, wherein the deformed shapes are cross-sectional shapes of the sidewalls.

15. The device of claim 13, wherein each of the sidewalls deforms in shape such that a cross-sectional shape of the inner lumen changes, thereby conforming the cross-sectional shape of the inner lumen to an outer diameter of the inner member.

16. The device of claim 13, wherein each of the sidewalls tapers from the proximal end of the outer member to the distal end of the outer member.

17. The device of claim 13, wherein the inner member is bioabsorbable and the outer member is bioabsorbable.

18. The device of claim 13, wherein the distal tip is a closed tip.

* * * * *